United States Patent [19]
Halpern

[11] Patent Number: 6,132,360
[45] Date of Patent: Oct. 17, 2000

[54] MAGNETIC STRETCHING OF MAGNETIZED NEURONS FOR SPINAL CORD OR PERIPHERAL NERVE REPAIR AND REGENERATION

[76] Inventor: Alan A. Halpern, 1400 Low Rd., Kalamazoo, Mich. 49008

[21] Appl. No.: 09/083,559

[22] Filed: May 22, 1998

[51] Int. Cl.[7] ............................................. A61N 1/00
[52] U.S. Cl. ...................................... 600/9; 128/898
[58] Field of Search ................. 600/9–15; 128/897–898, 128/899

[56] References Cited

U.S. PATENT DOCUMENTS

| | | |
|---|---|---|
| 2,153,889 | 4/1939 | Hames ........................................ 600/3 |
| 3,422,816 | 1/1969 | Robinson et al. ......................... 600/12 |
| 4,623,355 | 11/1986 | Sawruk . |
| 4,632,116 | 12/1986 | Rosen . |
| 4,662,884 | 5/1987 | Stensaas . |
| 4,754,745 | 7/1988 | Horowitz ................................... 600/3 |
| 4,774,967 | 10/1988 | Zanakis . |
| 4,863,668 | 9/1989 | Griffiths . |
| 4,869,247 | 9/1989 | Howard . |
| 4,870,966 | 10/1989 | Dellon . |
| 4,883,618 | 11/1989 | Barrows . |
| 4,889,478 | 12/1989 | Stensaas . |
| 4,919,140 | 4/1990 | Borgens . |
| 4,963,146 | 10/1990 | Li . |
| 5,011,486 | 4/1991 | Aebischer . |
| 5,019,087 | 5/1991 | Nichols . |
| 5,030,225 | 7/1991 | Aebischer . |
| 5,061,281 | 10/1991 | Mares . |
| 5,092,871 | 3/1992 | Aebischer . |
| 5,125,888 | 6/1992 | Howard . |
| 5,147,399 | 9/1992 | Dellon . |
| 5,358,475 | 10/1994 | Mares . |
| 5,487,897 | 1/1996 | Polson . |
| 5,556,428 | 9/1996 | Shah . |
| 5,584,885 | 12/1996 | Seckel . |
| 5,634,462 | 6/1997 | Tyler . |
| 5,654,332 | 8/1997 | Armistead . |
| 5,655,546 | 8/1997 | Halpern . |
| 5,656,605 | 8/1997 | Hansson . |
| 5,795,286 | 8/1998 | Fischell et al. ............................ 600/3 |

OTHER PUBLICATIONS

Lin et al., Biomechanics 28, No. 12, pp. 1429–1438 (1995).

*Primary Examiner*—Samuel G. Gilbert
*Attorney, Agent, or Firm*—The Firm of Gordon W. Hueschen

[57] ABSTRACT

A severed or otherwise interrupted spinal cord or peripheral nerve is provided with magnetic nanoparticles which are absorbed or actively incorporated into the neurons and their axons. The severed or otherwise interrupted nerve or cord is then exposed to an external magnetic field which is moved longitudinally of the severed or otherwise interrupted nerve or spinal cord, thereby stretching the magnetic particle-loaded neurons and their axons along the desired axis for bridging the gap or gaps and repairing the injured spinal cord or nerve. The procedure may be repeated to extend the area of repair. The severed or otherwise interrupted spinal cord or peripheral nerve is advantageously provided, either internally or alongside, with an insert comprising multiple strands of biodegradable material having magnetic particles oriented along the axis thereof, for focusing and concentrating the external magnetic field in the desired axis. Magnetic particles tagged with substances which are biologically incorporated into neurons and their axons may be employed to increase the absorption of the magnetic particles into the cells and/or to stimulate the growth activities of the cell.

12 Claims, 4 Drawing Sheets

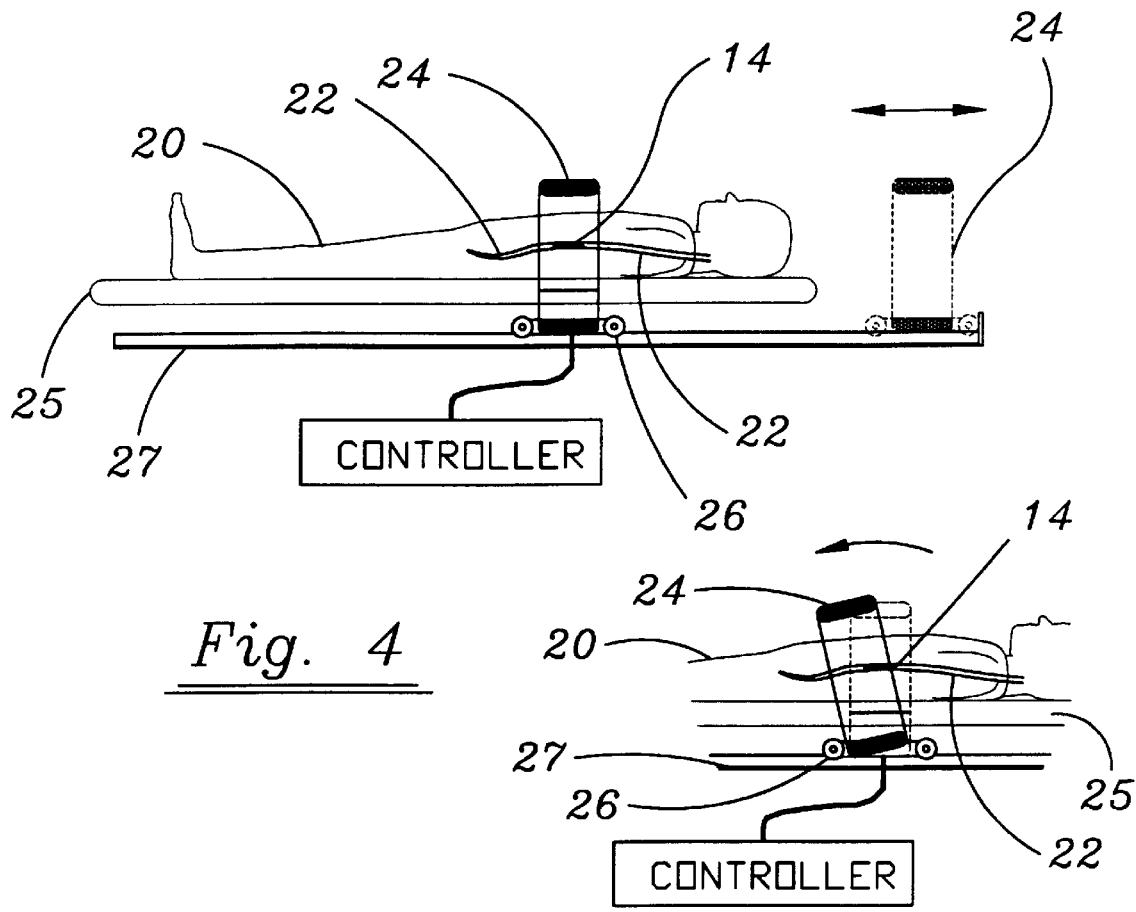
Fig. 4
Fig. 4A
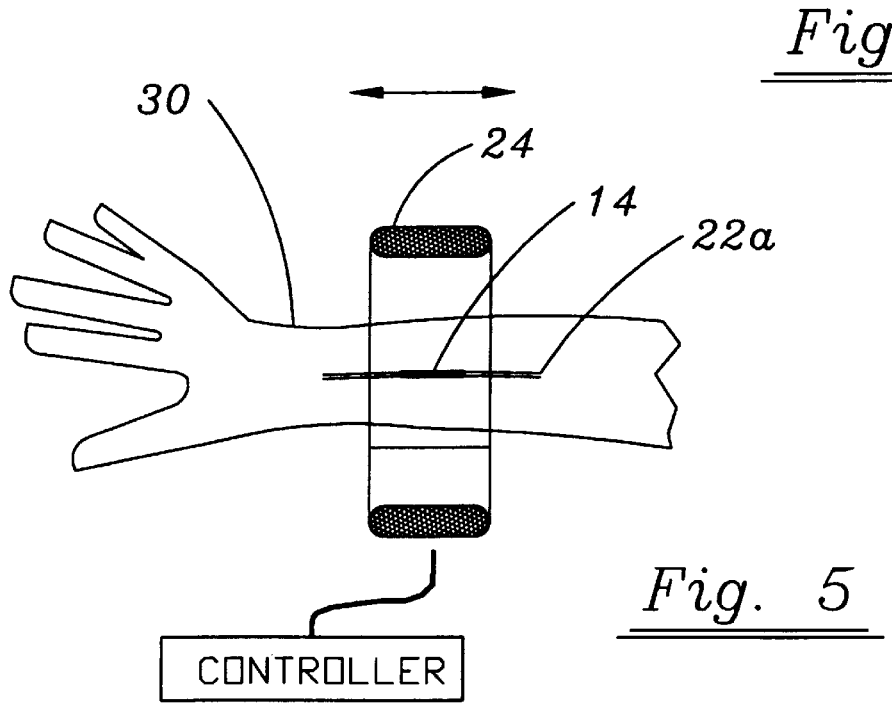
Fig. 5

MAGNETIC STRETCHING OF MAGNETIZED NEURONS FOR SPINAL CORD OR PERIPHERAL NERVE REPAIR AND REGENERATION

BACKGROUND OF THE INVENTION AND PRIOR ART

1. Field of the Invention

The present invention relates to the stretching of magnetic particle-impregnated neurons and their axons by means of an external magnetic field and the use of such procedure for bridging gaps in damaged spinal cords and peripheral nerves for their repair and regeneration.

2. Background of Invention

Despite significant advances in our understanding of neurophysiology and spinal cord injury, a patient who sustains a complete spinal cord injury has little hope of recovery. Previous research has not yet yielded a way to stimulate the neuronal axons to regrow to replace the injured axonal structures and re-unite them with the motor neuron and, similarly, to replace the sensory axonal structures and unite them with their corresponding target cells. In other words, there has been some success in stimulating nerves to sprout, but not in directing that limited growth in a specifically-desired direction. To date, the only clinically effective treatment has been that of pharmacologic modification of the injury process to prevent further secondary damage to the spinal cord following the acute phase of the spinal cord injury. Thus, in most cases, damage to the spinal cord means permanent paralysis. The advice given on a hieroglyphic found in a pyramid from 2,500 B.C. that "this is a condition that cannot be treated" remains unfortunately largely true despite great effort. In the United States, there are approximately 250,000 individuals with permanent spinal cord injury with about 10,000 new cases each year. Paraplegia affects 55% of the spinal cord injured population, while 44% are affected by quadriplegia. According to the American Paralysis Association, the initial hospitalization averages $140,000 with an average lifetime cost of $1.2 million, depending on the severity of injury and age at which injury occurred. Christopher Reeves, who recently sustained a severe spinal cord injury, reports that his care costs $550,000 per year. More than 60% of the spinal cord injured population were between the ages of 16 and 30. The majority, 90% of spinal cord injured individuals, survive and live near normal life spans.

The present methodology and technology is applicable to the repair of spinal cord severance, but may also be applied to other causes of neuronal interruption including myelodysplasia, damage from herniated nucleus pulposus, and interruption of spinal cord function due to tumors or infection, as well as to interrupted or severed peripheral nerves, including nerves of the brachial plexus.

3. Prior Art

The most closely-related art known to the inventor is his own previous work related to cartilage repair, represented by Halpern, U.S. Pat. No. 5,655,546 (1997), in which magnetically-tagged particles are taken up by chondrocytes and directed to a cartilage defect site by magnetic implants at that site; whereas Howard et al., U.S. Pat. No. 4,869,247 (1989) and Howard et al., U.S. Pat. No. 5,125,888 (1992) describe a system for the eradication of a tumor in which an electromagnetic field is positioned outside the body to deliver a small heat-sensitive pod or metal-tagged drug to any location in the brain or other body part. The small magnetic object, perhaps a ball, is inserted in the patient's head via a burr hole and magnetically manipulated to the tumor site. An energy beam is then directed at the magnetic object to accomplish destruction of the tumor. The metal-tagged drug is magnetically manipulated to a desired body part and the drug released by an energy beam which separates the drug from its magnetic counterpart; and Aebischer et al., U.S. Pat. No. 5,092,871 (1992) describe an electrically-charged nerve guidance channel for repairing severed nerve ends. In this device, the nerve ends are placed in proximity to each other within the lumen of the guidance channel, the idea being to promote repair.

See also the additional U.S. Patents and Publications listed on the attached Invention Disclosure Statement (IDS).

OBJECTS OF THE INVENTION

It is an object of the present invention to provide a method or procedure for the stretching of neurons and their axons, including the step of impregnating them with magnetic particles and then applying an external magnetic field for the stretching or elongation of the neurons and axons along a desired axis. In the literature on spinal cord injury, such a process has also been referred to as regeneration or repair. It is a further object to provide a method for the repair of interruptions or severances in the spinal cord and peripheral nerves by the loading of magnetic particles into neurons and their axons at the point of interruption or severance and applying an external magnetic field for the stretching or elongation of neurons and their axons for bridging of the gap or gaps in the area with the concurrent repair or regeneration of the damaged nerve or cord. It is an additional object of the invention to provide such a method wherein the external magnetic field is moveable along the axis in which it is desired that the neurons and their axons be stretched. It is a further object to provide a method and means for focusing or concentrating the external magnetic field along the desired axis of the nerve or spinal cord, either by the employment of magnetized substances which are actively incorporated into or complexed with the neurons or magnetized strands of biodegradable material which are implanted into or adjacent the nerve or spinal cord. Another object of the invention is to provide a single strand of biodegradable material in which magnetic particles are located either internally or externally, as well as a composite involving multiple such strands of biodegradable material for introduction by surgical intervention into the spinal cord or peripheral nerve or alongside and adjacent thereto for focusing or concentrating an external magnetic field at the point of severance or interruption and along the axis on which stretching of the neurons and their axons, by means of the application of an external magnetic field which is moveable along the axis in the direction in which stretching, is desired. Yet additional objects will become apparent hereinafter and still further objects will be apparent to one skilled in the art.

The foregoing and other objects, advantages, and characterizing features of the invention will become apparent from the following description of certain illustrative embodiments thereof considered together with the accompanying drawings, wherein like reference numerals signify like elements throughout the various figures to the extent feasible.

SUMMARY OF THE INVENTION

According to the invention, a clinically viable therapy for the repair of severances or interruptions in the spinal cord or peripheral nerves includes the introduction of ferromagnetic particles into the area of the interruption, which ferromagnetic particles are absorbed by or actively incorporated into the neurons and their axons and which are then subjected to a moveable external magnetic field directed longitudinally along the spinal cord or nerve in a continuous or a plurality of applications for stretching of the magnetic particle-loaded neurons and axons for bridging of the gap or gaps at the point of interruption and continuing for as long as desired or, specifically, until a desired bridging has been effected. The surgical implantation of strands of biodegradable material containing ferromagnetic areas into or alongside the spinal cord or nerve is a preferred manner of concentrating and focusing the external magnetic field into the area of interruption and along the axis of the spinal cord or peripheral nerve. Alternatively, such focusing or concentration may be effected by application, usually injection, of ferromagnetic particles which are complexed with substances which are actively incorporated into the severed end of a damaged spinal cord or peripheral nerve, i.e., by the neurons and their axons, and which substances may include, for example, horseradish peroxidase or neuroimmunophilin ligands for neuronal growth stimulation. The magnetic nanoparticles may also be bonded to active RNA or DNA strands which, when incorporated into the neuron, stimulate axonal growth which is then directed to the desired location by application of the external magnetic field. Upon movement of the magnetic field longitudinally along the spinal cord or nerve, the neurons and axons are stretched, gaps are bridged, and the nerve or spinal cord repaired and regenerated.

What I believe to be my invention, then, inter alia, comprises the following, singly or in combination, and is thus further defined as follows:

A composite comprising multiple strands of biodegradable material, each strand comprising magnetic particles in spaced intervals along said strand and oriented along the axis thereof either on the surface or internally of said strand, said strands being held together in a biodegradable matrix or mesh.

Moreover, a method for the bridging of a gap or gaps in a severed or interrupted spinal cord or peripheral nerve comprising the steps of providing or loading neurons and axons of said spinal cord or nerve in the area of the interruption or severance with magnetic nanoparticles, exposing said magnetic particle-loaded neurons and axons of the spinal cord or peripheral nerve in the area of such severance or interruption to an external magnetic field, and moving said external magnetic field along the axis of said spinal cord or peripheral nerve for stretching of the magnetic particle-loaded neurons and axons for bridging of said gap or gaps; such a method wherein the neurons and axons of said spinal cord or nerve are provided or loaded with magnetic nanoparticles in the area of the interruption or severance by injection of magnetic nanoparticles and causing said magnetic nanoparticles to be absorbed by said neurons and axons; such a method wherein said magnetic nanoparticles are complexed with or bonded to a substance which is taken up by the neurons and axons at the severed end of a damaged spinal cord or peripheral nerve and which is actively incorporated into the neurons and axons as a complex molecule; such a method wherein the magnetic nanoparticles are bonded to a substance selected from nerve growth factors, horseradish peroxidase, neurotrophic immunophylins, and active DNA or RNA strands; such a method wherein said magnetic nanoparticles are introduced into the neurons and axons by injection into the spinal canal intrathecally or at the site of the spinal cord or nerve interruption; such a method including the step of focusing and concentrating the external magnetic field along said axis; such a method wherein an insert, comprising a plurality of biodegradable strands comprising metallic particles in spaced intervals along said strands and oriented along the axis thereof either on the surface or internally of said strands, is surgically implanted along the axis of said spinal cord or nerve for focusing and concentrating the external magnetic field along said axis; such a method wherein said external magnetic field comprises a coil which is moveable longitudinally along the axis of the spinal cord or peripheral nerve to assist in such stretching and bridging; and such a method wherein the coil for creating the external magnetic field is adjustable so as better to follow and coincide with the angle of the spinal cord or peripheral nerve itself.

BRIEF DESCRIPTION OF THE DRAWINGS

Reference is now made to the drawings for a better understanding of the invention, wherein:

FIG. 4 is a view of a patient having a severed or otherwise interrupted spinal cord in supine position with a focusing and concentrating implant according to FIG. 2 at the point of severance of the spinal cord with a moveable coil for creating an external magnetic field surrounding the patient mounted for longitudinal movement along a track beneath the patient and being controlled by a computerized controller.

FIG. 4A is a variation of FIG. 4 depicting the external field coil adjusted to an angle less than the vertical to correspond to the angle of the spinal cord which at some points departs from the strictly horizontal.

FIG. 5 is a depiction of an arm of a patient having a severed or otherwise interrupted median nerve with an insert according to FIG. 2 at the point of severance, the arm of the patient being surrounded by an external coil again controlled by a computerized controller for directing the magnetic field longitudinally of the severed or otherwise interrupted nerve.

DESCRIPTION OF THE PREFERRED EMBODIMENTS

Uptake of Magnetic Nanoparticles by Central Nervous System Neurons

The purpose of this research was to demonstrate the ability of central nervous system neuronal cells to take up magnetic nanoparticles successful in vitro. For this study, nine (9) separate groups of nanoparticles were provided in vials which had been washed with double-distilled water to remove the surfactants. The particles were superparamagnetic and ranged in size from 250 nanometers to 100 nanometers. Each group of particles was spun to assess the dry weight, frozen with liquid nitrogen, vacuum dried, and then diluted with sterile water to provide a weight of 1 mcg/ml. The particles were then diluted in Dulbecco's modified eagle medium (Life Technologies). This modification consisted of the addition of the following to 500 ccs. of Dulbecco's modified eagle medium: 6.25 ccs. of sterile 1M HEPES (Gibbco), 2 ccs. of Proline stock (Sigma) (0.115 g dissolved in 10 ccs.), DMEM (no additives), 2.5 ccs. of filter-sterilized 10 mg/ccL-ascorbic acid stock (made fresh) (Sigma) (0.10 g dissolved in 10 ccs.), DMEM, 5 ccs. sterile 100× Pen-Strep (Gibbco), 50 ccs. of sterile serum (fetal bovine) to give a final medium of 12.5 mM HEPES, 0.1NEAA, 0.4 mML-Proline, 50 mg/L-ascorbic acid, 1× Pen-Strep and 10% serum. This is a representative growth supporting medium.

The individual wells of a Falcon 24-well tissue culture plate were then filled with a tissue culture of cell lined HCN-1A human cerebral cortical neuron (American type culture collection ATCC599386). The pellets were then resuspended and, under sterile conditions, with laminar flow, 0.1 ml of each of the different nanoparticle preparations placed in the well. These were then allowed to incubate and were examined microscopically.

Evaluation microscopically demonstrated optimal uptake of BSA (bovine serum albumin) coated 100-nanometer particles (Quantum Design, Inc., San Diego, Calif.), which demonstrated the maximum uptake by the neurons and the least clumping of particles. Application of a magnetic field to the surface of the culture wells demonstrated the ability to attract the cells containing the magnetic nanoparticles to a permanent magnet.

Human cortical CNS neurons are obtained from a normal source and are maintained as living cells by culturing under growth-promoting conditions in the usual manner.

The neurons are impregnated with magnetic particles such as magnetite ($Fe_3O_4$) or ferriferous oxide ($FeO.Fe_3O_4$ or $Fe(FeO_3)_2$), having a molecular weight of 231.5, or like magnetic particles which are absorbed by the neuron and its axons upon exposure to such metallic nanoparticles under growth-promoting conditions as set forth in the foregoing.

Figure 6:
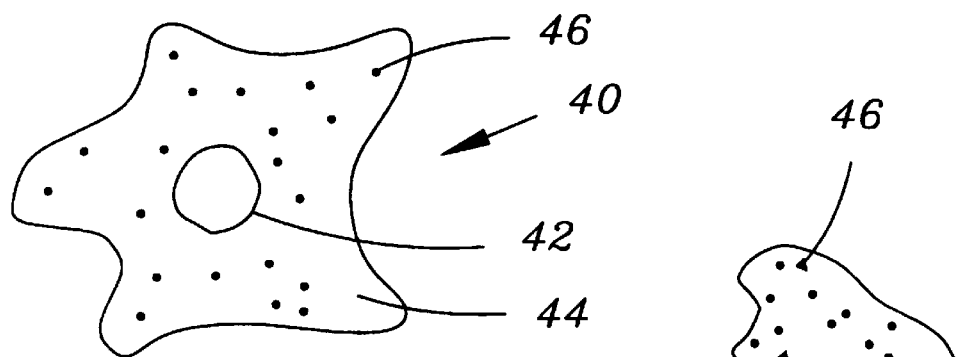
FIGS. 6 and 6A are drawings of a photomicrograph of a normal human cortical neuron or nerve cell having magnetic nanoparticles incorporated into the cell.
Figure 6A:
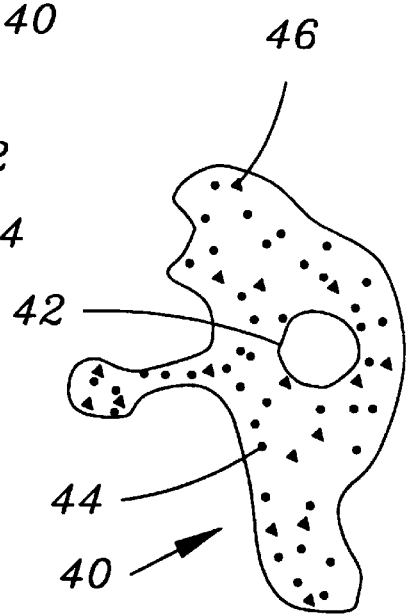

Such neurons are depicted in FIGS. 6 and 6A hereof. These are drawings of photomicrographs of the impregnated neurons. In FIGS. 6 and 6A these neurons are shown at 40, with their nuclei at 42 and their cell membrane 44 impregnated with absorbed ferromagnetic nanoparticles 46.

Figure 7:
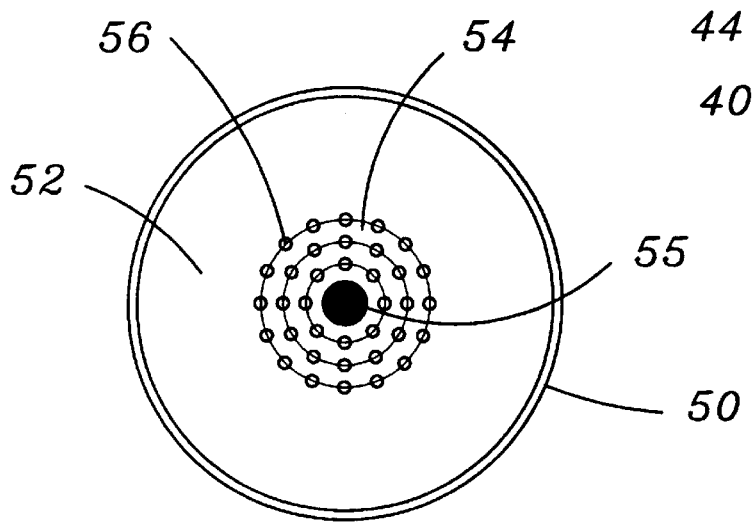
FIG. 7 is a Petri dish with normal growth-supporting medium therein, and a magnet placed at the center thereof. Concentric circles of a polylysine glue surround the central magnet, with magnetic nanoparticle-loaded human cortical neurons being placed in tissue culture at various points along the concentric circles of polylysine glue.

In FIG. 7 is shown an experiment involving a petri dish 50 replete with usual growth-promoting medium 52 and concentric circles of a polylysine glue 54 upon which ferromagnetic nanoparticle-loaded neurons in growth-promoting tissue culture 56 are spaced. In the center of the Petri dish 50 and in the center of the concentric circles of polylysine glue 54 is located magnet 55. This experiment was continued for a period of two (2) days and demonstrated that the magnetic particle-impregnated neurons 56 were actually drawn to the magnet and that the axons were elongated.

Figure 1:
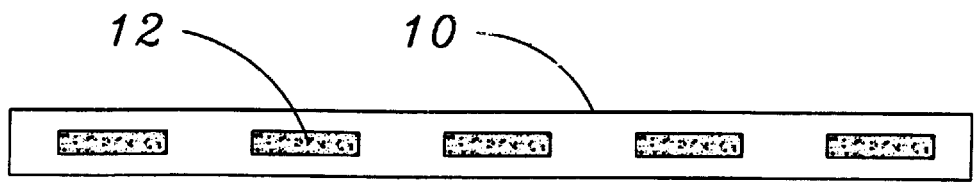
FIG. 1 is a top plan view of a single strand of biodegradable material having magnetic particles distributed therein or thereon and in any case oriented intermittently along the axis of the strand of biodegradable material.
Figure 8:
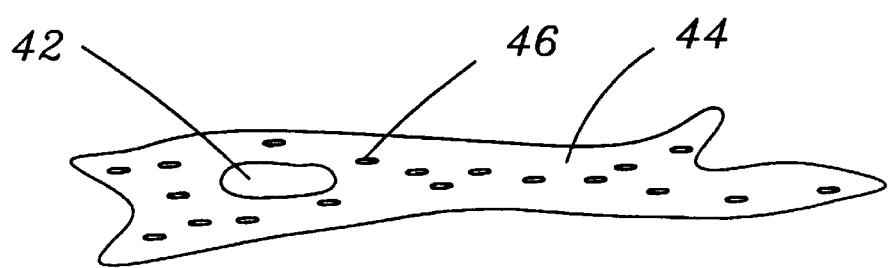
FIG. 8 is a drawing of a photomicrograph of a cortical neuron which has been exposed to the magnetic field created in the device of FIG. 7 and which has been stretched to create an elongated axon thereof by attraction of the magnetic nanoparticles in the cell membrane to the central magnet.

FIG. 8 is a drawing of a photomicrograph showing a magnetic particle-loaded neuron after exposure to the experiment illustrated in FIG. 7. At 40S is shown a neuron having its nucleus 42 and its cell membrane 44 with absorbed ferromagnetic particles 46 which has been stretched to create an elongated axon by application of the external magnetic field, namely, the magnet 55 in FIG. 7. The application of the foregoing knowledge into a useful clinical procedure is effected in the following manner:

As shown in FIG. 1, a single strand of biodegradable material, for example such as collagen, fibrin, or fibrin-collagen material, a bioresorbable polymer such as polylactic acid or polyglycolic acid or a composite of the two polymers, or the like, is provided with magnetic properties by orienting particles of ferromagnetic material in spaced relation along the axis thereof, either on the surface thereof, if necessary by means of an innocuous and physiologically-acceptable glue, or internally thereof as by providing a fine straw of biodegradable material and then intermittently providing areas of magnetic particles and glue along the interior thereof. Such a single strand of biodegradable material comprising magnetic particles oriented along the axis thereof is shown at 10, with the areas of magnetic particles being designated 12.

Figure 2:
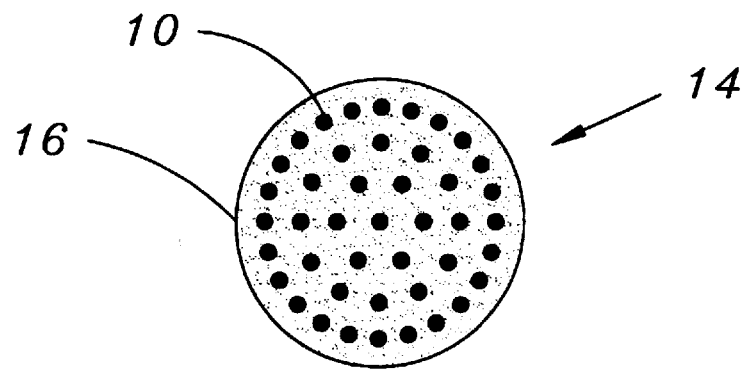
FIG. 2 is a composite comprising multiple strands according to FIG. 1 held together in a porous biodegradable matrix or mesh, which composite can be made or cut in varying lengths to comprise an "insert" for focusing and concentrating an external magnetic field into a selected area and along a selected axis.

Such strands may be combined to form a composite, as shown in FIG. 2. By positioning a plurality of such strands together longitudinally and holding them together by means of a biodegradable porous matrix or mesh, or simply by fusing them together, the composite 14 is formed, comprising a plurality of the individual strands 10 in a biodegradable matrix or mesh 16.

Such strands or composites can be made to various sizes or cut to various sizes, as desired. These can then be implanted in or alongside the spinal cord or peripheral nerve, such as the sciatic nerve, femoral nerve, or the median nerve of an arm, by surgical intervention.

Figure 3:
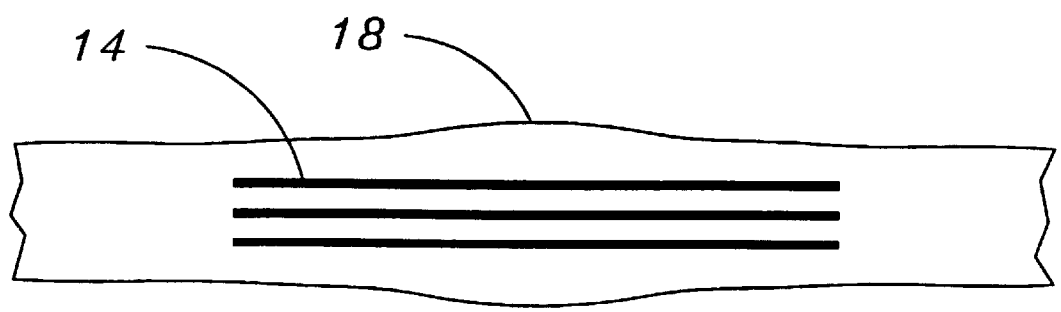
FIG. 3 is a depiction of a spinal cord or peripheral nerve into which have been implanted a series of implants according to FIG. 2.

The implantation of three (3) of these composites 14 into a nerve 18 is schematically shown in FIG. 3, the nerve in this case being uninterrupted.

In the simplistic drawing of FIG. 4, the subject is placed on a non-magnetic table and radiographic studies are taken to establish the orientation of the spinal canal and the location of the site of injury. Magnetic resonance imaging studies are done previously to establish the extent of the most severe injury. A motorized system is placed around the table controlling the travel and orientation of a superconducting electromagnetic coil. The supine patient 20 lies on a table 25 with super-conducting coils 24, which generate a large magnetic field, positioned about the patient 20 and mounted on a moveable truck 26 which is moveable along track 27. The interrupted spinal cord of the patient is shown at 22, with an insert of FIG. 2 therein or alongside being shown at 14 for focusing and concentrating the external magnetic field to the area and along the axis of the spinal cord. A computerized controller moves the magnetic field generated by coils 24 along the track 27 to direct the magnetic particles contained in the neurons and the neurons themselves and their axons in the desired longitudinal axis, as shown by the arrow.

In the variation of FIG. 4A, the coils 24 are shown in an angled position with respect to the vertical as altered by the computerized controller to direct the magnetic field somewhat from the horizontal so as to coincide with the deviation from the horizontal in the spinal cord itself. During the process the magnetized neurons and their axons are magnetically stretched longitudinally and thus bridge the gap or interruption in the spinal cord as the neurons and their axons are stretched longitudinally as in FIG. 8 and fused with other neurons.

X-rays are in any event taken prior to the procedure to establish the exact axis along which the magnetic coils 24 should be moved with respect to the spinal cord 22.

In FIG. 5 is depicted the employment of the procedure for treating an interrupted peripheral nerve, in this case the median nerve in the arm 30 of a patient, for which purpose the focusing and concentrating insert 14 is inserted at the point of interruption of the median nerve 22a, the external magnetic field again being provided by an external coil 24 surrounding the arm of the patient and the movement of which longitudinally with respect to the nerve is controlled by a computerized controller along the arrow-indicated axis.

Figure 9:
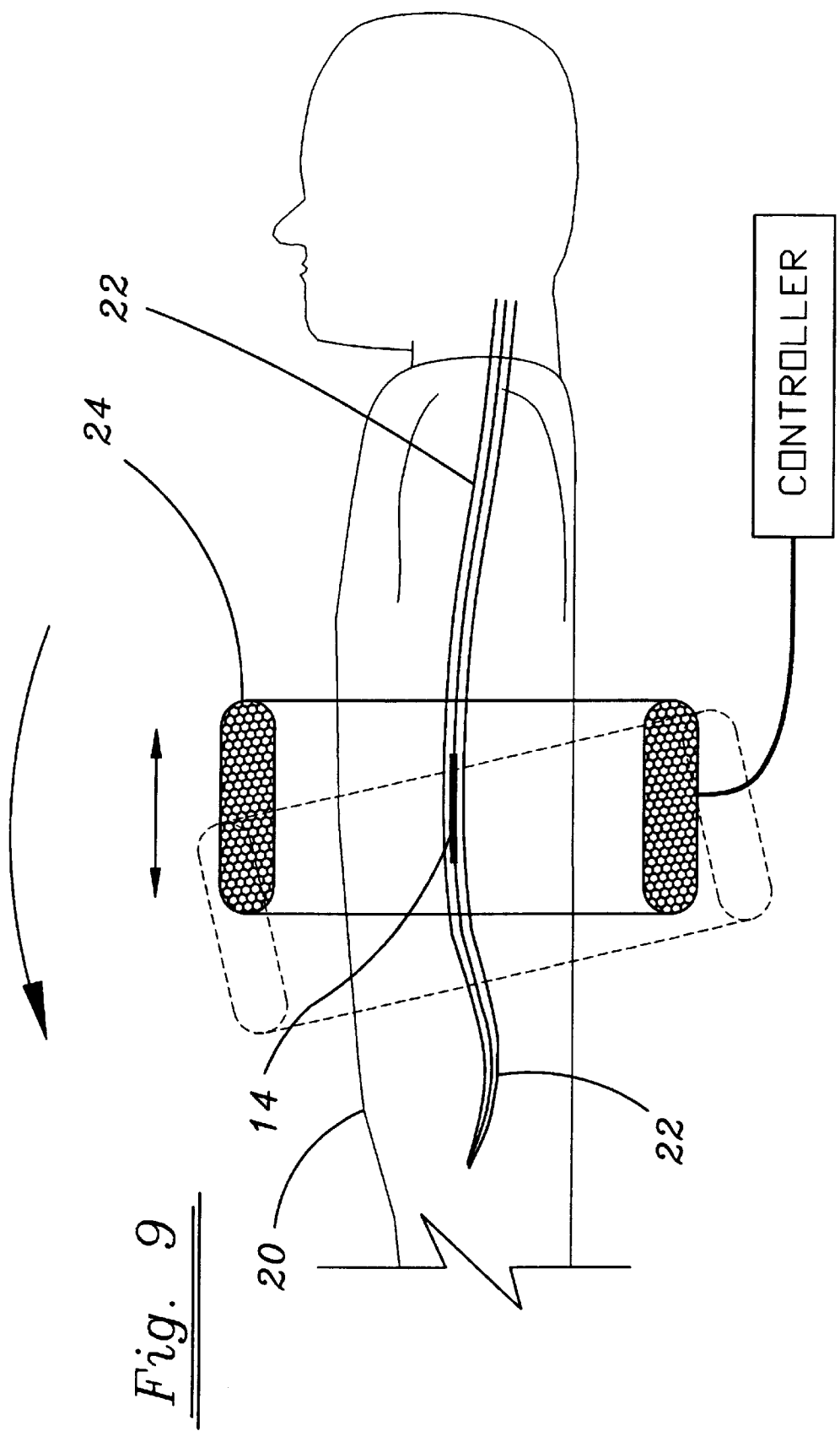
FIG. 9 is an enlarged version of FIG. 4, again showing the severed or otherwise interrupted spinal cord and a focusing and concentrating insert according to FIG. 2 at the point of severance thereof, with the external magnetic field coil controlled by a computerized controller for longitudinal movement along the patient's body and along the spinal cord with variations from the strictly perpendicular being available to conform with variations in the spinal cord as indicated in shadow lines similarly to FIG. 4A.

FIG. 9 is an enlarged depiction of the subject matter of FIG. 4, more adequately showing patient 20, the curvature of the interrupted spinal cord 22, and the focusing and concentrating insert 14 surgically implanted therein or alongside at the point of interruption thereof. As usual, the external magnetic field is provided by coils 24 controlled by a computerized controller, and in shadow lines is shown a variation from the perpendicular which may be effected by the controller so as better to follow the curvature of the spinal cord itself and ensure stretching of the magnetic particle-loaded neurons and their axons longitudinally along the exact axis desired, as determined by X-rays prior to the procedure.

OPERATION

According to the present invention, the subject or the relevant appendage thereof is placed on a non-magnetic table and radiographic studies conducted to establish the orientation of the spinal cord or peripheral nerve and the exact location of the site of injury.

Magnetic resonance imaging studies will have been carried out previously to establish the extent of the most severe injury.

A motorized system is then placed around the table controlling the orientation of a super-conducting electromagnetic coil for the establishment and control of the external magnetic field, the same being controlled by a computerized controller.

Magnetic nanoparticles are then injected into the spinal canal and/or directly into the rostral axons (closest to the brain) adjacent to the area of injury of the spinal cord, or adjacent to the injury of the peripheral nerve. These magnetic nanoparticles are preferably tagged to a neuronal growth factor or growth factors.

One or more composites comprising a plurality of biodegradable magnetic threads or strands comprising interrupted areas of ferromagnetic material therein or thereon so that the magnetic field can be advanced along the same (the "inserts" previously described) are implanted longitudinally along the axis of the spinal cord or into the spinal cord itself in the area or site of the primary injury, and preferably extending all the way to the site of the distal motor neurons. A surgical intervention is required for implantation or for opening up of the spinal canal for insertion of these biodegradable threads. The same procedure is employed when an interrupted peripheral nerve is involved.

The purpose of the biodegradable magnetic threads or strands is to concentrate or focus the external magnetic field along the course or axis of the spinal cord or peripheral nerve at and along the point of interruption thereof. The magnetic particles are in spaced relation along the strands so that the external magnetic field may be advanced and concentrated along their axis.

Small magnets may also be implanted longitudinally of the spinal cord or nerve so as to decrease the requirement for external magnetic force. Grouping must be avoided, i.e., aggregation at a single point on a single axis, so that such magnets must be spaced longitudinally just as the areas of ferromagnetic material are spaced in the biodegradable magnetic threads or strands.

The magnetic nanoparticles are introduced into the neurons by injection into the spinal canal intrathecally or at the site of the spinal cord or nerve interruption, where they are taken up or absorbed by the neurons and their axons, or in some cases intravenously and then concentrated and localized at the point of interruption of the spinal cord or nerve by the application of the external magnetic field (and "inserts" as desired or required), which is then in any case moved longitudinally of the spinal cord or nerve for stretching of the neurons and their axons.

Alternatively, the physician may employ magnetic nanoparticles which are processed with a substance which is taken up by the neurons and their axons upon injection and which is actively incorporated into the neurons to form a complex molecule. Such substances may include horseradish peroxidase, nerve growth factor, or neurotropic immunophilins for neuronal growth stimulation. Such bioabsorbable magnetic nanoparticles are then administered by direct injection into the injury site or intrathecal injection or intravenously and subsequent localization and concentration by application of the external magnetic field.

After preparation of the spinal cord or peripheral nerve site in the manner indicated, the patient is placed in the external magnetic field and the magnetic field gradually moved down the spine. Alternatively, the appendage of the patient with the interrupted peripheral nerve is placed in the magnetic field and the field gradually moved down the peripheral nerve. Classically, axons will grow only at about one (1) millimeter per day although, with the application of magnetic force to the magnetic particle-loaded neurons and their axons, this growth rate is accelerated.

The orientation of the external coil is maintained perpendicular to the orientation of the spinal cord or peripheral nerve although the orientation may be changed slightly from the vertical as the axons grow down the spinal cord. Such deviation from the perpendicular is generally not necessary when peripheral nerves are involved.

Periodically, assessment is made using radiographic studies to determine the localization of the magnetic particles. In the most sophisticated devices, this assessment can be built into the coil system so that localization of the magnetic particles can be checked and the coil adjusted and/or moved accordingly. In such a biofeedback type of system, the coil position is based on the progression of the magnetic particles and, accordingly, also of the neurons and axons containing the same.

When the problem is an interruption of the spinal cord, the further problem of sensory restoration can be addressed by injection of magnetic nanoparticles into the muscle adjacent to the peripheral nerves leading into the neurons of the spinal cord and into the cauda equina, the nerve roots at the bottom of the spinal cord, and/or the distal or bottom end of the spinal cord itself. Then, similar to the previous procedure outlined for the motor neurons, the magnetic field is applied to the spinal cord, but in this case the field is moved rostral or cephalad, that is, upwardly toward the head and not downwardly from the brain, to assist the axons in growing and/or stretching from the sensory nerve neurons in the spinal cord to the more central connection in the base of the brain.

For clarity, it should be understood that the motor neurons extend outwardly from the brain along the spinal cord whereas sensory nerves come into the neurons in the spinal cord and extend upwardly to the brain through the axons of the neurons. The axons are thus generally referred to as the nerve-cell processes or protuberances which conduct impulses away from the neuronal cell body.

It is thereby seen from the foregoing that the objects of the present invention have been accomplished and that a novel, efficient, and economic method and apparatus have been provided, all in accord with the Objects of the Invention and the Summary of Invention as set forth hereinbefore.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

I claim:

1. A composite comprising multiple strands of biodegradable material, each strand comprising magnetic particles in spaced intervals along said strand and oriented along an axis thereof either on a surface or internally of said strand, said strands being held together in a biodegradable matrix or mesh.

2. A method for the bridging of a gap or gaps in a severed or interrupted spinal cord or peripheral nerve comprising the steps of providing or loading neurons and axons of said spinal cord or nerve in an area of the interruption or severance with magnetic nanoparticles, exposing said magnetic particle-loaded neurons and axons of the spinal cord or peripheral nerve in the area of such severance or interruption to an external magnetic field, and moving said external magnetic field along an axis of said spinal cord or peripheral nerve for stretching of the magnetic particle-loaded neurons and axons for bridging of said gap or gaps.

3. The method of claim 2 wherein the neurons and axons of said spinal cord or nerve are provided or loaded with magnetic nanoparticles in the area of the interruption or severance by injection of magnetic nanoparticles and causing said magnetic nanoparticles to be absorbed by said neurons and axons.

4. The method of claim 2 wherein said magnetic nanoparticles are complexed with or bonded to a substance which is taken up by the neurons and axons at the severed end of a damaged spinal cord or peripheral nerve and which is actively incorporated into the neurons and axons as a complex molecule.

5. A method of claim 4 wherein the magnetic nanoparticles are bonded to a substance selected from the group consisting of nerve growth factors, horseradish peroxidase, neurotrophic immunophylins, and DNA or RNA strands.

6. The method of claim 5 wherein said magnetic nanoparticles are introduced into the neurons and axons by injection into the spinal canal intrathecally or at the site of the spinal cord or nerve interruption.

7. The method of claim 4 wherein said magnetic nanoparticles are introduced into the neurons and axons by injection into the spinal canal intrathecally or at the site of the spinal cord or nerve interruption.

8. The method of claim 2 wherein said magnetic nanoparticles are introduced into the neurons and axons by injection into the spinal canal intrathecally or at the site of the spinal cord or nerve interruption.

9. The method of claim 2 including the step of focusing and concentrating the external magnetic field along said axis.

10. The method of claim 9 wherein an insert, comprising a plurality of biodegradable strands comprising magnetic particles in spaced intervals along said strands and oriented along the axis thereof either on a surface or internally of said strands, is surgically implanted along an axis of said spinal cord or nerve for focusing and concentrating the external magnetic field along said axis.

11. The method of claim 2 wherein said external magnetic field is created by a coil which is moveable longitudinally along an axis of the spinal cord or peripheral nerve to assist in such stretching and bridging.

12. The method of claim 11 wherein the coil for creating the external magnetic field is adjustable so as better to follow and coincide with the angle of the spinal cord or peripheral nerve.

* * * * *

UNITED STATES PATENT AND TRADEMARK OFFICE
CERTIFICATE OF CORRECTION

PATENT NO. : 6,132,360
DATED : October 17, 2000
INVENTOR(S) : Alan A. Halpern, M.D.

It is certified that error appears in the above-identified patent and that said Letters Patent is hereby corrected as shown below:

Title page,
Item [56] References Cited, Item 12:
  "4,889,478  12/1989  Stensaas" should read:
  -- 4,889,478  10/1988  Stensaas --.

Signed and Sealed this

Thirtieth Day of October, 2001

Attest:

*Nicholas P. Godici*

NICHOLAS P. GODICI
*Acting Director of the United States Patent and Trademark Office*

*Attesting Officer*